United States Patent
Kumazawa et al.

(10) Patent No.: US 12,263,194 B2
(45) Date of Patent: Apr. 1, 2025

(54) BACILLUS BACTERIUM, INTERLEUKIN-22 PRODUCTION INDUCING AGENT, SKIN BARRIER FUNCTION ENHANCING AGENT

(71) Applicants: ICHIBIKI CO., LTD., Nagoya (JP); NATIONAL UNIVERSITY CORPORATION TOKYO MEDICAL AND DENTAL UNIVERSITY, Tokyo (JP)

(72) Inventors: Toshihiko Kumazawa, Toyohashi (JP); Atsuhisa Nishimura, Toyohashi (JP); Noriyuki Asai, Toyohashi (JP); Takahiro Adachi, Tokyo (JP)

(73) Assignees: ICHIBIKI CO., LTD., Nagoya (JP); NATIONAL UNIVERSITY CORPORATION TOKYO MEDICAL AND DENTAL UNIVERSITY, Tokyo (JP)

( * ) Notice: Subject to any disclaimer, the term of this patent is extended or adjusted under 35 U.S.C. 154(b) by 0 days.

(21) Appl. No.: 18/184,711

(22) Filed: Mar. 16, 2023

(65) Prior Publication Data

US 2023/0263841 A1 Aug. 24, 2023

Related U.S. Application Data

(63) Continuation of application No. 16/970,018, filed as application No. PCT/JP2019/005693 on Feb. 15, 2019, now abandoned.

(30) Foreign Application Priority Data

Feb. 16, 2018 (JP) .................................. 2018-026444

(51) Int. Cl.
*A61K 35/742* (2015.01)
*A61P 17/00* (2006.01)
*C12N 1/20* (2006.01)
*C12R 1/07* (2006.01)

(52) U.S. Cl.
CPC ............ *A61K 35/742* (2013.01); *A61P 17/00* (2018.01); *C12N 1/20* (2013.01); *C12N 1/205* (2021.05); *C12R 2001/07* (2021.05)

(58) Field of Classification Search
None
See application file for complete search history.

(56) References Cited

U.S. PATENT DOCUMENTS

2010/0297092 A1  11/2010  Farmer et al.

FOREIGN PATENT DOCUMENTS

| JP | 2012-525428 A | 10/2012 |
|---|---|---|
| JP | 5090754 B2 | 12/2012 |
| JP | 2019-141035 A | 8/2019 |

OTHER PUBLICATIONS

Yang, Gui-Yan et al., "Influence of orally fed a select mixture of Bacillus probiotics on intestinal T-cell migration in weaned MUC4 resistant pigs following Escherichia coli challenge," Vet. Res., 2016, vol. 47:71, pp. 1-15. (cited in the ISR).

Inooka, S et al., "The Effect of Bacillus natto on the T and B Lymphocytes from Spleens of Feeding Chickens," Poult. Sci., 1986, vol. 65, pp. 1217-1219. (cited in the ISR).

Kato, Takeo et al., "Growth of Nisin-Producing Lactococci in Cooked Rice Supplemented with Soybean Extract and its Application to Inhibition of Bacillus subtilis in Rice Miso," Biosci. Biotechnol. Biochem., 2001, vol. 65, No. 2, pp. 330-337. (cited in the ISR).

Kiuchi, Kan et al., "Isolation of Microorganisms from Specially Prepared Miso," Report of National Food Research Institute, No. 45, 1984, pp. 14-18. (English abstract and Tables are included) (cited in the ISR).

Majeed, Muhammed et al., "Role of probiotics for balanced skin microflora," Euro Cosmetics, 2015, pp. 10-11. (cited In the ISR).

International Search Report mailed Apr. 23, 2019, issued for PCT/JP2019/005693.

Olivia B. Parks et al., "Interleukin-22 Signaling in the Regulation of Intestinal Health and Disease", Frontiers in Cell and Developmental Biology, vol. 3, No. 85, Jan. 13, 2016, pp. 1-13. (cited in the Dec. 3, 2021 Search Report issued for EP19753824.2).

Muhammed Majeed et al., "Bacillus coagulans MTCC 5856 supplementation in the management of diarrhea predominant Irritable Bowel Syndrome: a double blind randomized placebo controlled pilot clinical study", Nutrition Journal, vol. 15, No. 1, Feb. 27, 2016, pp. 1-10. (cited in the Dec. 3, 2021 Search Report issued for EP19753824.2).

Masoumeh Azimirad et al., "Inhibition of Lipopolysaccharide-Induced Interleukin 8 in Human Adenocarcinoma Cell Line HT-29 by Spore Probiotics: B. coagulans and B. subtilis (natto)", Probiotics and Antimicrobial Proteins, vol. 9, No. 1, Oct. 26, 2016, pp. 56-63. (cited in the Dec. 3, 2021 Search Report issued for EP19753824.2).

European Search Report mailed Dec. 3, 2021, issued for European Patent Application No. 19753824.2.

Office Action mailed Jan. 24, 2023, issued for JP2019-026040 and machine English translation thereof.

G.-Y. Yang et al., "Influence of orally fed a select mixture of Bacillus probiotics on intestinal T-cell migration in weaned MUC4 resistant pigs following *Escherichia coli* challenge," Veterinary Research, 2016, pp. 1-15 (cited in the Jan. 24, 2023 DA issued for JP2019-026040).

Philip L. Simonian et al., "IL-17A-Expressing T Cells Are Essential for Bacterial Clearance in a Murine Model of Hypersensitivity Pneumonitis," J. Immunol., vol. 182, No. 10, 2009, pp. 6540-6549. (cited in the Jan. 24, 2023 OA issued for JP2019-026040).

(Continued)

*Primary Examiner* — Brian Gangle
(74) *Attorney, Agent, or Firm* — Troutman Pepper Locke LLP

(57) ABSTRACT

A *Bacillus* bacterium that induces the production of interleukin-22 is provided. The *Bacillus* bacterium that induces the production of interleukin-22.

6 Claims, 8 Drawing Sheets

Specification includes a Sequence Listing.

(56) References Cited

OTHER PUBLICATIONS

Muhammad Majeed et al., "Role of probiotics for balanced skin microflora," Euro Cosmetics, 2015, pp. 10-11. (cited in the Jan. 24, 2023 OA issued for JP2019-026040).

Office Action mailed Jun. 13, 2023, issued for JP2019-026040 and English translation thereof.

T. Onda et al., "Microbiological analysis for safe and high-quality miso-brew and research on lactic acid bacteria produced by Mycobacterium," Summary of the 11th Yamanashi Science Academy Award, 2008, p. 1-17.(cited in the Jun. 13, 2023 OA issued for JP2019-026040).

BACILLUS BACTERIUM, INTERLEUKIN-22 PRODUCTION INDUCING AGENT, SKIN BARRIER FUNCTION ENHANCING AGENT

TECHNICAL FIELD

The present invention relates to a *Bacillus bacterium*, an interleukin-22 production inducing agent, and a skin barrier function enhancing agent. More particularly, the present invention relates to *Bacillus bacterium* which induces the production of interleukin-22, an interleukin-22 production inducing agent, and a skin barrier function enhancing agent.

BACKGROUND ART

Currently, several types of interleukins, such as interleukin-10 and interleukin-12, are known as a group of cytokines, and interleukin-22 (IL-22) has also been reported as one of them.

This interleukin-22 is a cytokine belonging to the interleukin-10 family, and has been reported to have a function of enhancing a barrier function of skin, intestine, and the like, and is an important cytokine in improving the immune system.

Here, for example, in order to improve the immune function by increasing the production amount of interleukin-12, a functional food containing *Bacillus natto* (*Bacillus subtilis*), which is a kind of *Bacillus bacterium*, as an active ingredient has been reported (see Patent Document 1).

CITATION LIST

Patent Documents

[Patent Document 1] JP-B2-5090754

SUMMARY OF THE INVENTION

Problem to be Solved by the Invention

The functional food described in Patent Document 1 uses *Bacillus natto* (*Bacillus subtilis*) to increase the production amount of interleukin-12, and the effect of increasing (inducing) the production of interleukin-22 has not been reported.

Thus, there is a need to find a *bacterium* capable of inducing the production of interleukin-22, and in particular, there is a need for a *bacterium* that is easy to ingest.

The present invention provides a *Bacillus bacterium* that induces the production of interleukin-22.

Means for Solving the Problems

According to the present invention, there is provided a *Bacillus sp. bacterium* shown below.
- [1] A *Bacillus bacterium* that induces the production of interleukin-22.
- [2] The *Bacillus bacterium* described in [1], wherein the *Bacillus bacterium* has the potency to improve the viability of B cells and the activation potency of B cells.
- [3] The *Bacillus bacterium* described in [1] or [2], wherein the *Bacillus bacterium* is derived from foods.
- [4] The *Bacillus bacterium* described in any one of [1] to [3], wherein the *Bacillus bacterium* is derived from *miso* or *natto*.
- [5] The *Bacillus bacterium* described in any one of [1] to [4], wherein the *Bacillus bacterium* belongs to at least one selected from the group consisting of *Bacillus subtilis* and *Bacillus coagulans*.
- [6] The *Bacillus bacterium* described in any one of [1] to [5], wherein the *Bacillus bacterium* is a *Bacillus bacterium* of Accession number NITE BP-02583, a *Bacillus bacterium* of Accession number NITE BP-02584, or a *Bacillus bacterium* of Accession number NITE BP-02590.
- [7] An interleukin-22 production inducing agent containing the *Bacillus bacterium* described in any one of [1] to [6].
- [8] A skin barrier function enhancing agent containing the *Bacillus bacterium* described in any one of [1] to [6].

Effect of the Invention

The *Bacillus bacterium* of the present invention induces the production of interleukin-22, and can be an active ingredient of an interleukin-22 production inducing agent used for prevention of diseases caused by insufficient production of interleukin-22.

The interleukin-22 production inducing agent of the present invention induces the production of interleukin-22, and can be an active ingredient of an interleukin-22 production inducing agent used for prevention of a disease caused by insufficient production of interleukin-22.

MODE FOR CARRYING OUT THE INVENTION

Figure 1:
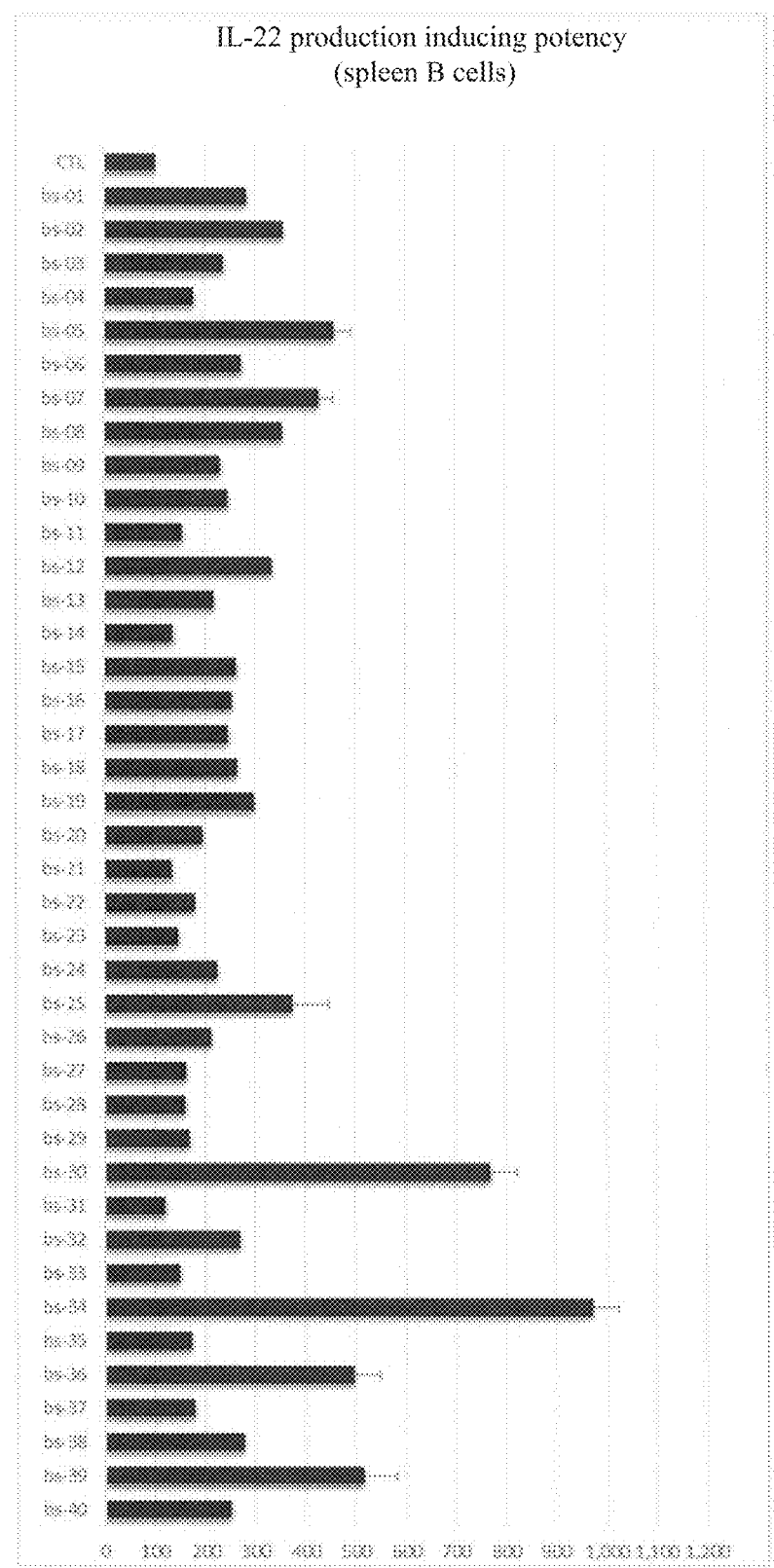
FIG. 1 is a graph showing the screening results of strains with the production inducing potency of interleukin-22 in B cells.
Figure 2:
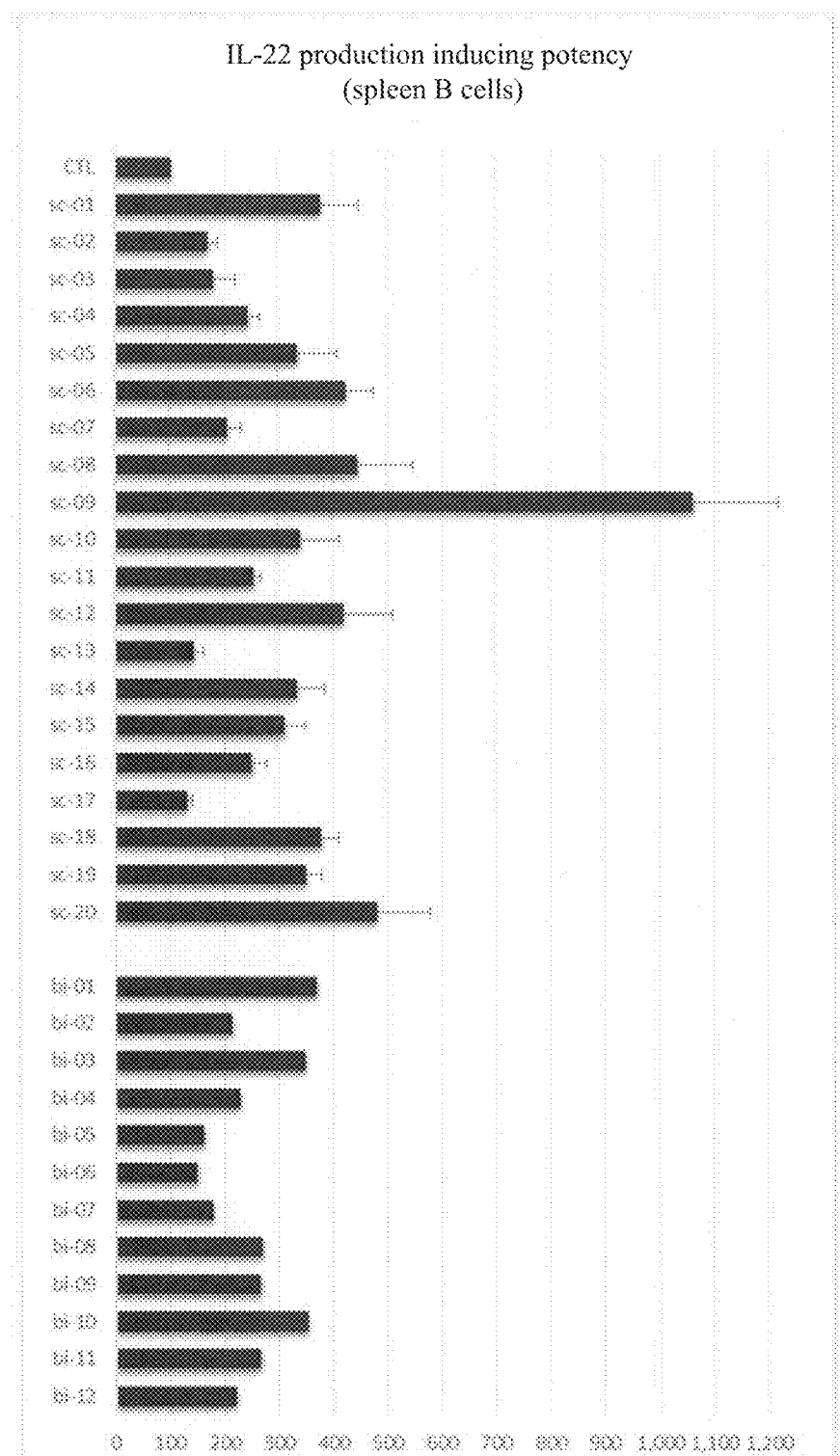
FIG. 2 is a graph showing the screening results of strains with the production inducing potency of interleukin-22 in B cells.
Figure 3:
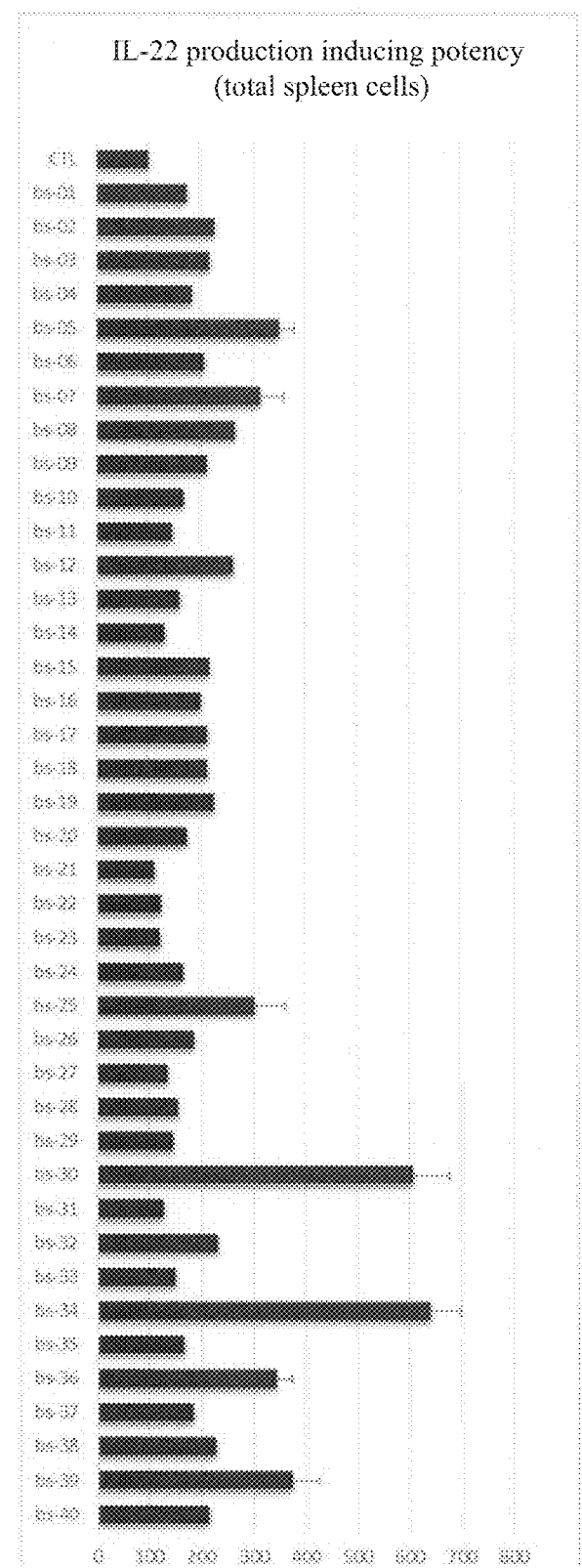
FIG. 3 is a graph showing the screening results of strains with the production inducing potency of interleukin-22 in total spleen cells.
Figure 4:
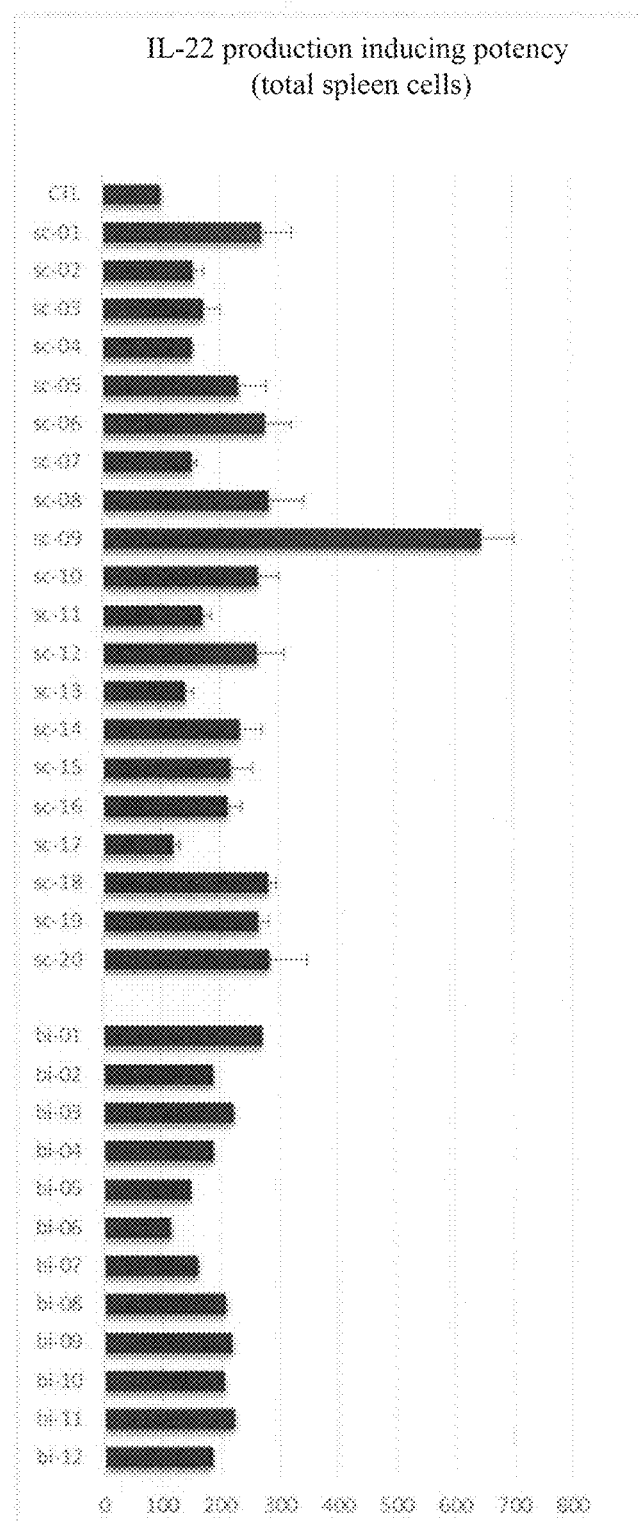
FIG. 4 is a graph showing the screening results of strains with the production inducing potency of interleukin-22 in total spleen cells.
Figure 5:
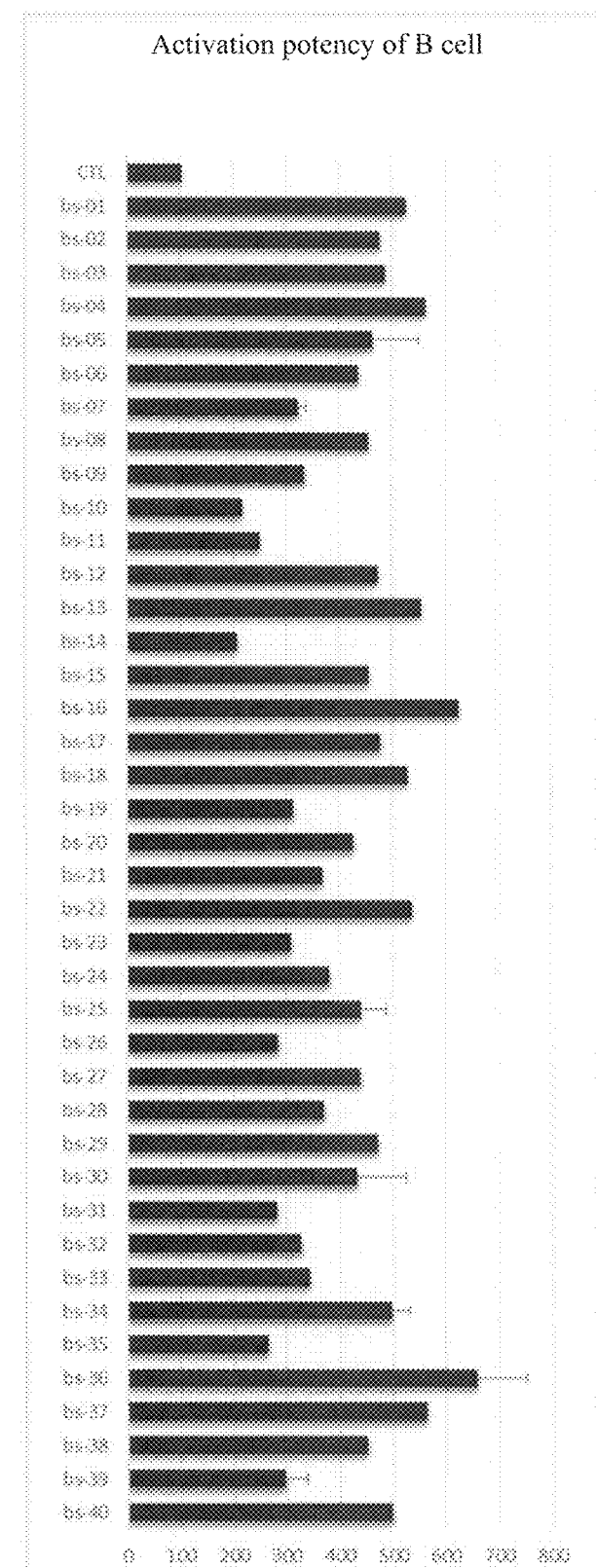
FIG. 5 is a graph showing the activation potency of B cells.
Figure 6:
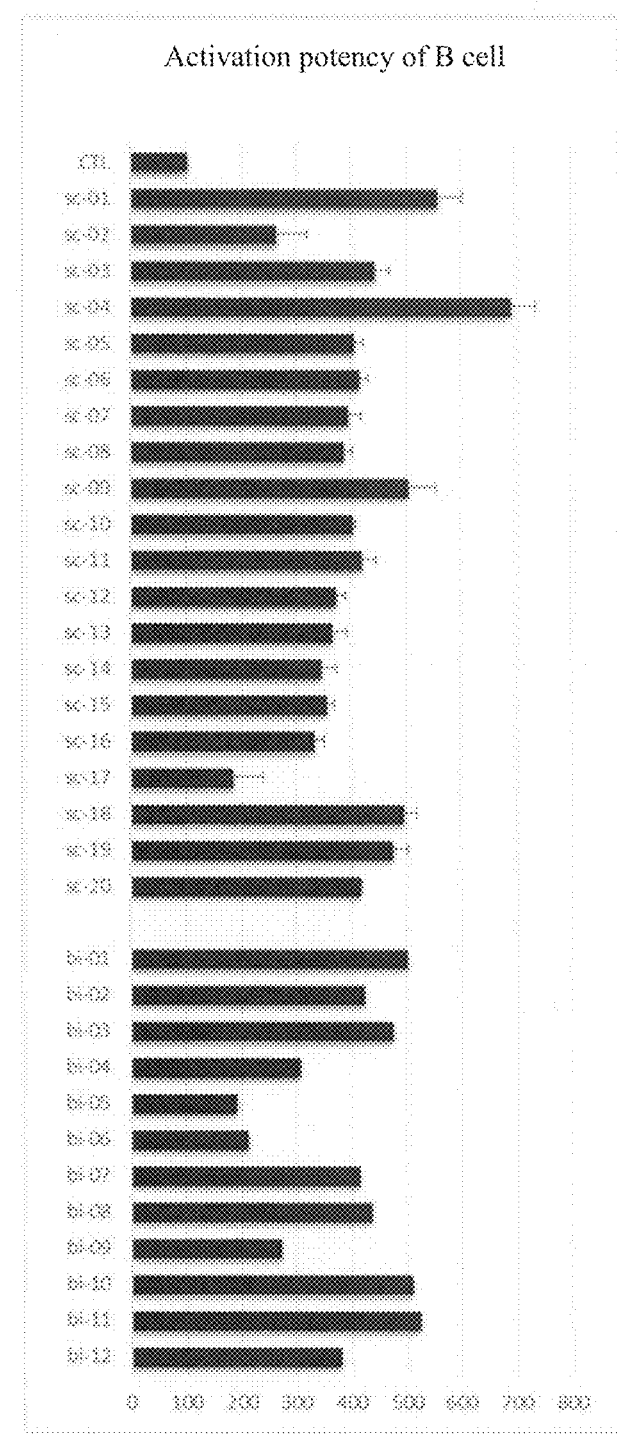
FIG. 6 is a graph showing the activation potency of B cells.

Hereinafter, modes for carrying out the present invention will be described, but the present invention is not limited to the following embodiments. That is, it should be understood that those in which changes, improvements, and the like, have been appropriately added to the following embodiments based on the ordinary knowledge of a person skilled in the art without departing from the gist of the present invention fall within the scope of the present invention.

[1] *Bacillus bacterium*

The *Bacillus bacterium* of the present invention induces the production of interleukin-22 (IL-22). Here, for example,

*Bacillus subtilis*, which is a kind of *Bacillus bacterium*, is a microorganism that has long been involved in the Japanese diet, and for example, in the production (fermentation) of *natto*, which is a traditional fermented food of Japan, *Bacillus natto*, which is a kind of *Bacillus subtilis*, is involved. In addition, moromi (main fermenting mash) of *miso* and soy sauce often contain *Bacillus subtilis*, and *Bacillus subtilis* has been consumed by eating these fermented foods. Thus, for example, *Bacillus subtilis* has the advantages that it is safe to ingest (i.e., highly suitable for food) and it is easily produced since its culturing is easy. *Bacillus* is an aerobic spore-bearing *bacterium*, and the typical species is *Bacillus subtilis*. *Bacillus natto* is classified as a type of *Bacillus subtilis*.

Since "interleukin-22" can proliferate keratinized cells to promote skin turnover, it can be expected to be suitably used for applications such as skin care materials and antibacterial materials. In addition, interleukin-22 is involved in tissue repair, cell survival and proliferation, and mucosal barrier protection, and can be expected to have usages such as prevention and treatment of skin diseases such as atopic dermatitis, and the like, fatty liver disease, and infectious diseases caused by such as *Clostridium difficile*.

Furthermore, it is preferable that the *Bacillus bacterium* of the present invention has the potency to improve the viability of B cells and the activation potency of B cells.

Here, B cells play a central role in humoral immunity and are the only cells capable of producing antibodies against foreign bodies (antigens) such as pathogens, but are not known for their action by *Bacillus bacterium* such as *Bacillus subtilis*. In addition, B cells, which are cells that present antigen to T cells, are known to be indispensable cells for maintenance of activated T cells. Therefore, strengthening the action of B cells reinforces an action of T cells, and also strengthens the immunostimulatory effect in the entire cells of the immune system. In the present invention, the "activation potency of B cells" means that both the potency of antibody production and the potency of antigen presentation are activated.

Then, if it is possible to achieve a direct control such as artificial reinforcement of action of B cells capable of producing antibodies to attack foreign bodies, it can be expected to lead to the prevention, alleviation, or treatment of immune system diseases such as allergic diseases, infectious diseases, and autoimmune diseases, having an effect on the action by the antibody.

As used herein, "having the potency to improve the viability of B cells" means having the property of enhancing the "viability" of B cells. More specifically, it means that when a ratio of the number of viable B cells to the total number of cells in a sample to which *Bacillus bacterium* is not added using experimental mouse spleen cells is defined as a reference (reference value 100), a value (measured value) of the ratio of the number of viable B cells to the total number of cells in a sample to which *Bacillus bacterium* is added is more than 100. The "total number of cells" can be quantitatively determined by flow cytometry. Cells that react with an anti-B220 antibody are referred to as B cells, the "number of viable B cells (living cells)" is determined by quantifying cells not stained with Propidium Iodide (PI) nucleus staining liquid, but react with the anti-B220 antibody.

Note that "having the viability of B cells" is as described above, but specifically, it means that a value (measured value) obtained by a method shown in Example 2 is more than 100.

As used herein, "having an activation potency of B cells" means having the potency (property) to activate B cells. More specifically, it means that when a ratio of the number of activated B cells to the number of unactivated B cells in a sample to which *Bacillus bacterium* is not added using experimental mouse spleen cells is defined as a reference (reference value 100), a value (measured value) of the ratio of the number of activated B cells to the number of unactivated B cells in a sample to which *Bacillus bacterium* is added is more than 100. The "number of activated B cells" is determined by measuring the number of cells reacting with both the anti-B220 antibody and an anti-CD86 antibody by flow cytometry. The "number of unactivated B cells" is determined by measuring the number of cells reacting with the anti-B220 antibody without reacting with the anti-CD86 antibody by flow cytometry.

Note that "having an activation potency of B cells" is as described above, but specifically, it means that a measured value obtained by a method shown in Example 1 is more than 100.

The *Bacillus bacterium* of the present invention may be derived from foods, and specifically, may be derived from *miso* or derived from *natto*. Such microorganisms derived from foods (especially fermented foods) that have been eaten since ancient times provide even greater safety when ingested.

Here, the *Bacillus bacterium* derived from *miso* may be *Bacillus bacterium* such as *Bacillus subtilis* isolated in the brewing process of *miso*. The *Bacillus bacterium* "isolated in the brewing process of *miso*" refers to *Bacillus bacterium* fixed in "Kura (storage)" "Muro (chamber)," and "Oke (tub)" in the brewing process of *miso*. Furthermore, it refers to *Bacillus bacterium* which can grow (survive) from the preparation to the ripening process of *miso*. Note that, in the present invention, *Bacillus bacterium* derived from *miso* are not limited to those directly isolated in the brewing process of *miso*, but also include those isolated from *miso* and subsequently cultured (subcultured). *Bacillus bacterium* (*Bacillus subtilis*) derived from *natto* can be called *Bacillus bacterium* isolated in the manufacturing process of *natto*, and also includes *Bacillus subtilis* (*Bacillus bacterium*) isolated from commercial (product) *natto*.

The *Bacillus bacterium* of the present invention may belong to at least one selected from the group consisting of *Bacillus subtilis* and *Bacillus coagulans*. *Bacillus subtilis* and *Bacillus coagulans* (one of the spore-bearing *lactobacillus*) are microorganisms that have long been involved in Japanese diet and are safe to ingest (i.e., highly suitable for food). In addition, these have an advantage in that they are easily produced since their culturing is easy.

[1-1] Preferred *Bacillus bacterium*

The *Bacillus bacterium* of the present invention is preferably a *Bacillus bacterium* (strain) (strain name "sc-09") of Accession number NITE BP-02583 (hereinafter sometimes referred to as "*Bacillus coagulans* sc-09"), a *Bacillus bacterium* (strain name "bs-30") of Accession number NITE BP-02584 (hereinafter sometimes referred to as "*Bacillus subtilis* bs-30") or a *Bacillus bacterium* (strain name "bs-34") of Accession number NITE BP-02590 (hereinafter sometimes referred to as "*Bacillus subtilis* bs-34").

These *Bacillus* bacteria are derived from *miso*, so they are highly safe when ingested, and can directly act on B cells to exert viability and activation potency in B cells, thereby activating the immune system (i.e., they have a good immunostimulatory effect). Furthermore, these *Bacillus bacterium* have excellent production inducing potency of IL-22. These *Bacillus* bacteria may act on T cells, and may also act on dendritic cells and the like.

Here, the *Bacillus bacterium* of Accession number NITE BP-02583, the *Bacillus bacterium* of Accession number NITE BP-02584, and the *Bacillus bacterium* of Accession number NITE BP-02590 are all deposited with the National Institute of Technology and Evaluation Patents and Microorganisms Depositary (NPMD).

As described above, the *Bacillus bacterium* of the present invention is preferably the *Bacillus bacterium* of Accession number NITE BP-02583, the *Bacillus bacterium* of Accession number NITE BP-02584, or the *Bacillus bacterium* of Accession number NITE BP-02590, and the *Bacillus bacterium* of Accession number NITE BP-02583 is more excellent production inducing potency of IL-22.

Among the "preferable *Bacillus bacterium*", the *Bacillus bacterium* (strain name "sc-09") of Accession number NITE BP-02583 is *Bacillus coagulans* derived from *miso*, and is excellent in IL-22 production inducing potency. In other words, it is most preferable to employ it when it is desired to enhance the production of IL-22. In addition, the *Bacillus coagulans* sc-09 can be cultivated under anaerobic conditions and can grow in a high temperature range (45° C. to 60° C.). Therefore, it can be selectively cultivated in a high temperature range (45° C. to 60° C.) where it is difficult for common bacteria to grow. Moreover, it can be produced in a simple cultivation facility. In addition, because of its sporulation potency, it is easy to handle spawn (starter), such as storing them, by sporulating them.

Among the "preferred *Bacillus bacterium*", the *Bacillus bacterium* (strain name "bs-30") of Accession number NITE BP-02584 and the *Bacillus bacterium* (strain name "bs-34") of Accession number NITE BP-02590 are both *Bacillus subtilis* derived from *miso*, and can vigorously grow in environments with good air permeability at room temperature of about 25° C. to 45° C. Further, it can be grown even at a salinity of about 7 w/v %, and by culturing in a medium containing salinity, it is possible to suppress the growth of common bacteria, so that it is easily produced. In other words, it can be said that the production by a simple culture facility is possible. In addition, because of its sporulation potency, it is easy to handle spawn (starter), such as storing them, by sporulating them.

Therefore, it is also preferable that the *Bacillus bacterium* of the present invention is a *bacterium* capable of growing at a high temperature (45° C. or higher, more preferably 50° C. or higher). Being able to cultivate at high temperatures makes the culturing easier because other germs are less likely to be mixed in (less likely to be contaminated by other germs) as described above.

[2] Method of Preparing of *Bacillus bacterium*

The *Bacillus bacterium* of the present invention can be prepared by culturing, followed by a treatment such as sterilization, or the like. Specifically, after completion of the culturing, the medium component is removed by means such as centrifugation, or the like, followed by washing and purification. Then, heat sterilization is performed, and then drying and concentration are performed by means such as lyophilizing, reduced pressure drying, and hot air drying, and the like. In this way, *Bacillus bacterium* of the present invention can be prepared.

Note that, although there is no particular limitation on the heat sterilization, specifically, autoclave sterilization (121° C., 20 minutes) or the same degree of sterilization is preferable.

[3] Interleukin-22 (IL-22) Production Inducers

IL-22 production inducing agent of the present invention contains the *Bacillus bacterium* of the present invention. The IL-22 production inducing agent is capable of inducing the production of IL-22. Note that some *Bacillus* bacteria are conventionally eaten with fermented food, such as *Bacillus subtilis*, and some of them are highly safe, and therefore, when *Bacillus subtilis* or the like is used, IL-22 production inducing agent of the present invention can be highly safe.

In the IL-22 production inducing agent of the present invention, there is no particular limitation on the content ratio as long as it contains the *Bacillus bacterium* of the present invention as an active ingredient. Note that IL-22 production inducing agent of the present invention may contain indigestible dextrins, oligosaccharides, dextrins, silicon dioxide, and the like as other components in addition to the *Bacillus bacterium* of the present invention.

Note that the IL-22 production inducing agent of the present invention may include a culture, a bacterial cell (which may be either a vegetative cell or a spore), or a bacterial component, obtained when the *Bacillus* bacteria of the present invention is cultured.

Note that IL-22 production inducing agent of the present invention may itself be used as a food and drink, a supplement, a medicine, or the like, or may be added to a food and drink, a supplement, a medicine, or the like and used. There are no particular limitation for food and drinks, and the food and drinks may include, for example, *miso*, instant *miso* soup, cooked *miso* (processed *miso*), name-*miso* such as Kinzanji *miso*, soy sauce, soup, season sauce, seasoning sauce, seasoning for rice, side dishes, and sweet rice drinks (yeast drinks).

[4] Skin Barrier Function Enhancing Agent

The skin barrier function enhancing agent of the present invention contains *Bacillus bacterium* of the present invention. The skin barrier function enhancing agent can induce the production of IL-22 and suppress transepidermal water loss. That is, the tight junction of the skin epithelium become stronger and the barrier function of the skin can be enhanced (i.e., improved). When the barrier function of the skin is improved in this way, it is possible to keep the skin moist and to make it difficult to cause dry skin and sensitive skin. In addition, the skin can be protected from external stimulus such as invasion of pathogens (other external stimulus are, for example, stimulation by exposure to ultraviolet rays, stimulation by contact with allergens, chemicals, dust, and the like, and stimulation by exposure to a dry environment).

Here, the epidermal layer of the skin has a barrier function of protecting the living body from the above-mentioned external stimulus such as ultraviolet rays, allergens, chemicals, pathogens, and the like, but if the tight junction of the skin epithelium is loosened and the barrier function of the epithelial layer does not function sufficiently, it becomes impossible to protect the skin from the external stimulus. As a result, it causes problems such as rough skin, stains, wrinkles, deterioration of tenseness, and flabbiness of the skin. For this reason, it is important to keep the barrier function of the skin normal and to improve the barrier function when the function is deteriorated. By containing the

*Bacillus bacterium* of the present invention, the skin barrier function enhancing agent of the present invention induces the production of IL-22 by the *Bacillus bacterium* so that the barrier function of the skin is exhibited (an effect of preventing transepidermal water loss is exhibited).

Incidentally, when the amount of water loss from the transepidermis is large (that is, when the amount of TransEpidermal Water Loss (TEWL) is large), in addition to the skin (particularly, the epidermal layer) becomes dry, a sufficient protective function by the skin is not exhibited, and external stimulus such as ultraviolet rays, allergens, chemicals, and pathogens adversely affects the inside of the skin (occurrence of stains, itching, and the like).

EXAMPLES

Hereinafter, the present invention will be specifically described based on Examples, but the present invention is not limited to these Examples.

Example 1

(Measurement Test for IL-22)

*Bacillus* bacteria were collected from *miso* and *natto*, respectively, and the collected bacteria of the *Bacillus* bacteria were cultured and sterilized, and then added to an experimental mouse (C57BL/6) spleen cells and cultured, and the production amount of IL-22 was measured after culturing. The strains used in the tests are shown in Tables 1 and 2. Hereinafter, measurement test for IL-22 will be described in detail.

(1) Isolation and Identification of *Bacillus bacterium*:

*Bacillus* bacteria was collected from *miso* and *miso* brewing process, and *Bacillus* bacteria were also isolated from commercial *natto*. For the isolation medium, standard agar medium (manufactured by Nissui Pharmaceutical Co., Ltd.) was used, and it was cultured statically at 30° C. and 45° C. on for 1 to 2 days, and the bacteria were purely isolated from the obtained colonies to collect. In addition, in order to selectively obtain a *Bacillus coagulans*, a Lactobacilli MRS Agar (manufactured by Wako Pure Chemical Corporation) to which calcium carbonate was added was used, and cultured anaerobically at 50° C. for 1 to 3 days to collect colonies in which the surrounding calcium carbonate was dissolved.

The isolated *Bacillus* bacteria were subjected to Gram staining and observed with a microscope to confirm that they were Gram stained positive *bacillus* and whether they formed spores.

In addition, DNA was extracted from the isolated bacterial cell, and 16S rDNA was amplified by PCR using primer 10F as shown in SEQ ID NO: 1 and primer 1500R as shown in SEQ ID NO: 2, and then the bacterial species were identified by sequence analyses of the obtained PCR products. Details of the analysis method were based on the Japanese Pharmacopoeia 17th Edition reference information "Rapid identification method of microorganisms by gene analysis".

The collected *Bacillus* bacteria were 72 strains, of which 40 strains of *Bacillus subtilis* (including *Bacillus natto*) and 20 strains of *Bacillus coagulans* were included.

(2) Preparation of Bacterial Cell Suspension (Suspension of the *Bacillus bacterium*):

The isolated and identified *Bacillus* bacteria were cultured by shaking at 30° C. for 1 to 3 days using Nutrient Broth medium (manufactured by Wako Pure Chemical Corporation). However, as *Bacillus coagulans*, Lactobacilli MRS Broth (manufactured by Wako Pure Chemical Corporation) was used and cultured statically at 50° C. for 1 to 3 days.

After culturing, the cultures were subjected to autoclave sterilization at 121° C. for 20 minutes to obtain culture broth for each strain.

Next, each of the obtained cultures was centrifuged at 5000 rpm for 10 minutes. Thereafter, each of them was collected, washed 3 times with distilled water, and then suspended in distilled water and lyophilized to obtain a bacterial cell. Thereafter, each of the obtained bacterial cells was suspended in a phosphate buffer solution (PBS) of pH6.8 to a concentration of 1 mg/mL to prepare a bacterial cell suspension of each strain.

(3) Preparation of Cell Suspension:

Cells collected from the spleen of experimental mouse (C57BL/6) were collected in 50 ml conical tubes (manufactured by FALCON), and 5 mL of erythrocyte dissolving buffer (0.155M $NH_4Cl$, 0.01M Tris-HCl, pH7.5) was added to suspend the cells. Thereafter, 5 mL of phosphate buffer solution (PBS) of pH6.8 was added to this and centrifuged at 1200 rpm for 5 minutes. Thereafter, cells were washed twice with phosphate buffer solution (PBS) of pH6.8 to prepare cell suspension.

(4) Cell Culture:

The cell suspension was adjusted with the basic medium so as to be $2 \times 10^6$ cells/mL, and 1 mL of the adjusted cell suspension was seeded in a 24-well microplate (manufactured by FALCON) to obtain $2 \times 10^6$ cells/1 mL/well. Note that the basic medium was prepared by adding fetal bovine serum (manufactured by SAFC Biosciences) which was inactivated by heating at 55° C. for 30 minutes, to RPMI 1640 with a predetermined 0.3 g/L L-glutamic acid added (manufactured by Nacalai Tesque, Inc.), so as to be 9 (w/v) % in a medium. The above "RPMI 1640 with a predetermined 0.3 g/L L-glutamic acid added" is RPMI 1640 with a L-glutamic acid (0.3 g/L) added with a penicillin-streptomycin mixed solution (100 U/mL-100 μg/mL in a medium, manufactured by Nacalai Tesque, Inc.) and a 2-mercaptoethanol (50 μM in a medium, manufactured by Nacalai Tesque, Inc.)

After that, 10 μL of each bacterial cell suspension (1 mg/mL) was added and cultured at 37° C. and 5% $CO_2$ for 2 days. A control was also prepared. This control was prepared by culturing cells for 2 days without adding bacterial cell suspension to the adjusted cell suspension under the same conditions (37° C., 5% $CO_2$) as when the bacterial cells were added.

(5) Measurement of IL-22:

After culturing for 42 hours during culturing for 2 days (48 hours), 0.67 μL of BD GolgiStop (manufactured by BD) was added to the culture liquid and mixed. Thereafter, the culture liquid was further cultured at 37° C. and 5% $CO_2$ for 6 hours.

Thereafter, the cell culture liquid cultured in a 24-well microplate (manufactured by FALCON) was transferred to a 1.5 mL reaction tube (manufactured by Greiner Bio-One), centrifuged at 1200 rpm for 5 minutes, and the cells were collected. After that, the collected cells were fixed and permeated by using BD Cytofix/Cytoperm™ Fixation/Permeabilization Kit (manufactured by BD). This procedure followed the instructions attached to Fixation/Permeabilization Kit.

For staining of B cells, violetFluor450-labeled anti-B220 antibody (manufactured by TONBO Biosciences) was used, and further, for staining of IL-22, PE-labeled anti-IL-22 antibody (manufactured by affymetrix eBioscience) was used. In addition, APC-labeled anti-CD86 antibody (manufactured by TONBO Biosciences) was used to measure the activation status of B cells.

Staining reaction was performed by being left to stand for 60 minutes in refrigerator (5° C.). Thereafter, the mixture was centrifuged at 1200 rpm for 5 minutes, and the cells were collected and suspended in 0.5 mL of PBS to obtain a measuring sample.

Note that the measurement was performed using flow cytometry (MACSQuant Analyzer manufactured by Milteny Biotec)

For the analysis, FCS data analysis software FlowJo (manufactured by FlowJo, LLC) was used.
(Results)
(1) Measurement of IL-22-Producing Cell Amount in Spleen B Cells:

B220 positive cells were regarded as B cells, and the ratio of IL-22 positive cells in spleen B cells (IL-22$^+$, B220$^+$/B220$^+$) was determined for the respective measuring samples.

The percentage of IL-22 positive cells in B cells in the control (to which no bacterial cell suspension was added) was defined as the standard (100), and the relative values of the respective measuring samples were calculated to obtain the values of IL-22-producing cell amounts of B cells (in Tables 1 and 2, described as "IL-22 production inducing potency (spleen B cells)".

Mean value ($\bar{X}$) and standard error (S.E.) were obtained by measuring respective measuring samples once, and then repeating the measurement 2 to 6 times for the measuring samples having the high measurement values. The results are shown in Table 1 and Table 2.
(2) Measurement of IL-22-Producing Cell Amount in Total Spleen Cells:

The percentage of IL-22 positive cells in total spleen cells ("IL-22 positive cells/total spleen cells") was determined for respective measuring sample.

The percentage of IL-22 positive cells in spleen cells in the control (to which no bacterial cell suspension was added) was defined as the standard (100), and the relative values of the respective measuring samples were calculated to obtain the values of IL-22-producing cell amounts of total spleen cells (in Tables 1 and 2, described as "IL-22 production inducing potency (total spleen cells)".

In the same manner as "(1) Measurement of IL-22-producing cell amount in spleen B cells" above, the mean value ($\bar{X}$) and the standard error (S.E.) were obtained by measuring the respective measuring samples once, and then further repeating the measurement for the measuring samples having the high measurement values in the same manner as in (1) above. The results are shown in Table 1 and Table 2.
(3) Measurement of Activation Potency of B Cell:

The percentage of CD86 positive cells in B cells (CD86$^+$, B220$^+$/CD86$^-$, B220$^+$) was determined. Then, the percentage of CD86 positive cells in B cells in the control (to which no bacterial cell suspension was added) was defined as a reference (100), and the activation potency of B cells was calculated (in Tables 1 and 2, described as "Activation potency of B cells").

The measurement of the activation potency of the B cells was similarly repeated for the measuring samples obtained by repeating the above "(1) Measurement of IL-22-producing cell amount in spleen B cells" and "(2) Measurement of IL-22-producing cell amount in total spleen cells", and the mean values ($\bar{X}$) and the standard error (S.E.) were obtained. The results are shown in Table 1 and Table 2.
(4) Confirming of the Growth Temperature:

In addition, the growth temperature of each isolated strain was confirmed. Specifically, a medium obtained by putting 10 mL each of Nutrient Broth medium (manufactured by Wako Pure Chemical Corporation) into a test tube (diameter 18 mm×180 mm) and capped with a culture stopper (SILI-COSEN, manufactured by Shin-Etsu Polymer Co., Ltd.) and sterilized with an autoclave (121° C., 20 minutes) was prepared. A loopful of colonies were respectively inoculated into three media, and cultured statically at 30° C., 45° C., and 55° C., respectively. As a control, a medium that was not ingested bacteria was prepared. Visual confirmation (confirmation of turbidity of the medium and presence or absence of precipitation) was performed after 2 days of culture to determine whether or not the culture had grown sufficiently. The determination criteria was "O" for the case of proliferation, and "X" for the case of non-proliferation.

The results of confirmation of the growth temperature are shown in Table 1 and Table 2 (shown in the column of "Culture temperature" in Table 1 and Table 2). Both strains proliferated in cultures at 30° C.

TABLE 1

| Strain name | IL-22 production inducing potency (spleen B cells) | | IL-22 production inducing potency (total spleen cells) | | Activation potency of B cell | | Number of n | Isolated from | Culturing temperature | | |
|---|---|---|---|---|---|---|---|---|---|---|---|
| | $\bar{X}$ | S.E. | $\bar{X}$ | S.E. | $\bar{X}$ | S.E. | | | 30° C. | 45° C. | 55° C. |
| control | 100 | — | 100 | — | 100 | — | 1 | — | — | — | — |
| *Bacillus subtilis* (natto) bs-01 | 282 | — | 173 | — | 525 | — | 1 | natto | O | O | X |
| *Bacillus subtilis* (natto) bs-02 | 355 | — | 227 | — | 474 | — | 1 | natto | O | O | X |
| *Bacillus subtilis* (natto) bs-03 | 236 | — | 217 | — | 485 | — | 1 | natto | O | O | X |
| *Bacillus subtilis* (natto) bs-04 | 176 | — | 183 | — | 561 | — | 1 | natto | O | O | X |
| *Bacillus subtilis* (natto) bs-05 | 457 | 37 | 351 | 30 | 460 | 90 | 4 | natto | O | O | X |
| *Bacillus subtilis* (natto) bs-06 | 271 | 1 | 207 | — | 434 | — | 1 | natto | O | O | X |
| *Bacillus subtilis* (natto) bs-07 | 427 | 31 | 313 | 47 | 321 | 18 | 4 | natto | O | O | X |

TABLE 1-continued

| Strain name | IL-22 production inducing potency (spleen B cells) | | IL-22 production inducing potency (total spleen cells) | | Activation potency of B cell | | Number of n | Isolated from | Culturing temperature | | |
|---|---|---|---|---|---|---|---|---|---|---|---|
| | X⁻ | S.E. | X⁻ | S.E. | X⁻ | S.E. | | | 30° C. | 45° C. | 55° C. |
| *Bacillus subtilis* (natto) bs-08 | 353 | — | 266 | — | 453 | — | 1 | natto | ○ | ○ | X |
| *Bacillus subtilis* (natto) bs-09 | 230 | — | 211 | — | 333 | — | 1 | natto | ○ | ○ | X |
| *Bacillus subtilis* (natto) bs-10 | 245 | — | 166 | — | 215 | — | 1 | natto | ○ | ○ | X |
| *Bacillus subtilis* (natto) bs-11 | 154 | — | 145 | — | 248 | — | 1 | natto | ○ | ○ | X |
| *Bacillus subtilis* (natto) bs-12 | 332 | — | 261 | — | 471 | — | 1 | natto | ○ | ○ | X |
| *Bacillus subtilis* bs-13 | 218 | — | 160 | — | 553 | — | 1 | miso | ○ | ○ | X |
| *Bacillus subtilis* bs-14 | 135 | — | 130 | — | 206 | — | 1 | miso | ○ | ○ | X |
| *Bacillus subtilis* bs-15 | 262 | — | 216 | — | 453 | — | 1 | miso | ○ | ○ | X |
| *Bacillus subtilis* bs-16 | 252 | — | 199 | — | 622 | — | 1 | miso | ○ | ○ | X |
| *Bacillus subtilis* bs-17 | 245 | — | 211 | — | 475 | — | 1 | miso | ○ | ○ | X |
| *Bacillus subtilis* bs-18 | 262 | — | 211 | — | 526 | — | 1 | miso | ○ | ○ | X |
| *Bacillus subtilis* bs-19 | 298 | — | 224 | — | 311 | — | 1 | miso | ○ | ○ | X |
| *Bacillus subtilis* bs-20 | 193 | — | 172 | — | 424 | — | 1 | miso | ○ | ○ | X |
| *Bacillus subtilis* bs-21 | 133 | — | 110 | — | 366 | — | 1 | miso | ○ | ○ | X |
| *Bacillus subtilis* bs-22 | 178 | — | 122 | — | 535 | — | 1 | miso | ○ | ○ | X |
| *Bacillus subtilis* bs-23 | 145 | — | 120 | — | 307 | — | 1 | miso | ○ | ○ | X |
| *Bacillus subtilis* bs-24 | 223 | — | 164 | — | 378 | — | 1 | miso | ○ | ○ | X |
| *Bacillus subtilis* bs-25 | 372 | 74 | 302 | 60 | 437 | 51 | 4 | miso | ○ | ○ | X |
| *Bacillus subtilis* bs-26 | 211 | — | 186 | — | 282 | — | 1 | miso | ○ | ○ | X |
| *Bacillus subtilis* bs-27 | 161 | — | 135 | — | 436 | — | 1 | miso | ○ | ○ | X |
| *Bacillus subtilis* bs-28 | 159 | — | 154 | — | 369 | — | 1 | miso | ○ | ○ | X |
| *Bacillus subtilis* bs-29 | 166 | — | 145 | — | 470 | — | 1 | miso | ○ | ○ | X |
| *Bacillus subtilis* bs-30 | 766 | 55 | 605 | 72 | 430 | 96 | 4 | miso | ○ | ○ | X |
| *Bacillus subtilis* bs-31 | 118 | — | 126 | — | 280 | — | 1 | miso | ○ | ○ | X |
| *Bacillus subtilis* bs-32 | 267 | — | 230 | — | 325 | — | 1 | miso | ○ | ○ | X |
| *Bacillus subtilis* bs-33 | 147 | — | 149 | — | 341 | — | 1 | miso | ○ | ○ | X |
| *Bacillus subtilis* bs-34 | 971 | 53 | 638 | 60 | 495 | 38 | 4 | miso | ○ | ○ | X |
| *Bacillus subtilis* bs-35 | 171 | — | 166 | — | 262 | — | 1 | miso | ○ | ○ | X |
| *Bacillus subtilis* bs-36 | 494 | 54 | 342 | 32 | 655 | 96 | 4 | miso | ○ | ○ | X |
| *Bacillus subtilis* bs-37 | 176 | — | 183 | — | 561 | — | 1 | miso | ○ | ○ | X |
| *Bacillus subtilis* bs-38 | 275 | — | 226 | — | 449 | — | 1 | miso | ○ | ○ | X |
| *Bacillus subtilis* bs-39 | 513 | 68 | 372 | 56 | 294 | 44 | 4 | miso | ○ | ○ | X |
| *Bacillus subtilis* bs-40 | 249 | — | 213 | — | 496 | — | 1 | miso | ○ | ○ | X |

TABLE 2

| Strain name | IL-22 production inducing potency (spleen B cells) | | IL-22 production inducing potency (total spleen cells) | | Activation potency of B cell | | Number of n | Isolated from | Culturing temperature | | |
|---|---|---|---|---|---|---|---|---|---|---|---|
| | X⁻ | S.E. | X⁻ | S.E. | X⁻ | S.E. | | | 30° C. | 45° C. | 55° C. |
| control | 100 | — | 100 | — | 100 | — | — | — | — | — | — |
| *Bacillus coagulans* sc-01 | 376 | 70 | 272 | 52 | 555 | 46 | 3 | miso | ○ | ○ | ○ |
| *Bacillus coagulans* sc-02 | 168 | 20 | 155 | 20 | 262 | 58 | 3 | miso | ○ | ○ | ○ |
| *Bacillus coagulans* sc-03 | 179 | 43 | 173 | 30 | 441 | 29 | 3 | miso | ○ | ○ | ○ |
| *Bacillus coagulans* sc-04 | 243 | 22 | 152 | 4 | 688 | 48 | 3 | miso | ○ | ○ | ○ |
| *Bacillus coagulans* sc-05 | 334 | 75 | 232 | 47 | 404 | 19 | 5 | miso | ○ | ○ | ○ |
| *Bacillus coagulans* sc-06 | 423 | 54 | 276 | 48 | 414 | 17 | 5 | miso | ○ | ○ | ○ |
| *Bacillus coagulans* sc-07 | 204 | 28 | 152 | 11 | 392 | 27 | 3 | miso | ○ | ○ | ○ |
| *Bacillus coagulans* sc-08 | 444 | 104 | 284 | 60 | 385 | 17 | 5 | miso | ○ | ○ | ○ |
| *Bacillus coagulans* sc-09 | 1,062 | 158 | 643 | 60 | 501 | 53 | 7 | miso | ○ | ○ | ○ |
| *Bacillus coagulans* sc-10 | 338 | 75 | 264 | 38 | 400 | 8 | 5 | miso | ○ | ○ | ○ |
| *Bacillus coagulans* sc-11 | 253 | 16 | 172 | 15 | 417 | 27 | 3 | miso | ○ | ○ | ○ |
| *Bacillus coagulans* sc-12 | 419 | 90 | 263 | 47 | 371 | 18 | 5 | miso | ○ | ○ | ○ |
| *Bacillus coagulans* sc-13 | 143 | 19 | 141 | 15 | 364 | 27 | 3 | miso | ○ | ○ | ○ |
| *Bacillus coagulans* sc-14 | 332 | 54 | 234 | 39 | 343 | 31 | 5 | miso | ○ | ○ | ○ |
| *Bacillus coagulans* sc-15 | 309 | 41 | 218 | 37 | 353 | 17 | 5 | miso | ○ | ○ | ○ |

TABLE 2-continued

| Strain name | IL-22 production inducing potency (spleen B cells) | | IL-22 production inducing potency (total spleen cells) | | Activation potency of B cell | | Number of n | Isolated from | Culturing temperature | | |
|---|---|---|---|---|---|---|---|---|---|---|---|
| | X⁻ | S.E. | X⁻ | S.E. | X⁻ | S.E. | | | 30° C. | 45° C. | 55° C. |
| *Bacillus coagulans* sc-16 | 249 | 29 | 213 | 25 | 330 | 20 | 5 | miso | ○ | ○ | ○ |
| *Bacillus coagulans* sc-17 | 131 | 10 | 120 | 11 | 182 | 58 | 3 | miso | ○ | ○ | ○ |
| *Bacillus coagulans* sc-18 | 376 | 35 | 282 | 15 | 493 | 25 | 3 | miso | ○ | ○ | ○ |
| *Bacillus coagulans* sc-19 | 349 | 31 | 265 | 20 | 474 | 28 | 3 | miso | ○ | ○ | ○ |
| *Bacillus coagulans* sc-20 | 480 | 100 | 283 | 64 | 415 | 4 | 5 | miso | ○ | ○ | ○ |
| *Bacillus amyloliquefaciens* bi-01 | 369 | — | 270 | — | 499 | — | 1 | miso | ○ | ○ | X |
| *Bacillus amyloliquefaciens* bi-02 | 213 | — | 188 | — | 422 | — | 1 | miso | ○ | ○ | X |
| *Bacillus benzoevorans* bi-03 | 348 | — | 223 | — | 473 | — | 1 | miso | ○ | X | X |
| *Bacillus benzoevorans* bi-04 | 228 | — | 188 | — | 304 | — | 1 | miso | ○ | X | X |
| *Bacillus firmus* bi-05 | 161 | — | 149 | — | 189 | — | 1 | miso | ○ | X | X |
| *Bacillus megaterium* bi-06 | 148 | — | 115 | — | 209 | — | 1 | miso | ○ | ○ | X |
| *Bacillus megaterium* bi-07 | 176 | — | 161 | — | 412 | — | 1 | miso | ○ | ○ | X |
| *Bacillus megaterium* bi-08 | 267 | — | 209 | — | 434 | — | 1 | miso | ○ | ○ | X |
| *Bacillus megaterium* bi-09 | 264 | — | 219 | — | 270 | — | 1 | miso | ○ | ○ | X |
| *Bacillus novalis* bi-10 | 351 | — | 206 | — | 507 | — | 1 | miso | ○ | ○ | X |
| *Bacillus pumilus* bi-11 | 264 | — | 223 | — | 522 | — | 1 | miso | ○ | X | X |
| *Bacillus tequilensis* bi-12 | 219 | — | 185 | — | 378 | — | 1 | miso | ○ | X | X |

(5) Screening Results of IL-22-Producing Inducer:

The results of screening for each bacterial species were as follows (see Table 1. Table 2. FIGS. 1-6).

IL-22 production increased (more than 1.1 times) in all strains (72 strains). Among these, *Bacillus* bacteria derived from *miso* (for example, shown as the strain name of "bs-30", "bs-34" and "sc-09" in Table 1) showed 7-10 times the amount of IL-22-producing cells among B cells compared to the control, and the results for total spleen cell showed about 6 times the amount of IL-22-producing cells compared to the control. Strains with particularly large amount of IL-22-producing cells are shown in Table 3.

TABLE 3

| Strain name | IL-22 production inducing potency (spleen B cells) | | IL-22 production inducing potency (total spleen cells) | | Activation potency of B cell | | Isolated from |
|---|---|---|---|---|---|---|---|
| | X⁻ | S.E. | X⁻ | S.E. | X⁻ | S.E. | |
| *Bacillus subtilis* bs-30 | 766 | 55 | 605 | 72 | 430 | 96 | miso |
| *Bacillus subtilis* bs-34 | 971 | 53 | 638 | 60 | 495 | 38 | miso |
| *Bacillus coagulans* sc-09 | 1,062 | 158 | 643 | 60 | 501 | 53 | miso |

Summary

It was found that IL-22 was induced by stimulation of bacterial cell (sterilized *bacterium*) of *Bacillus bacterium*, and the degree of induction varied depending on the strains. *Bacillus bacterium* was considered to have IL-22 production inducing potency.

Although it is known that CD4⁺ T cells and NK cells produce IL-22, it has not been reported that IL-22 is produced in B cells. In addition, from the above results, when the *Bacillus* bacteria of the present invention were used, IL-22 production in spleen cells, in particular, from B cells was increased by stimulation of the bacteria.

Figure 7:
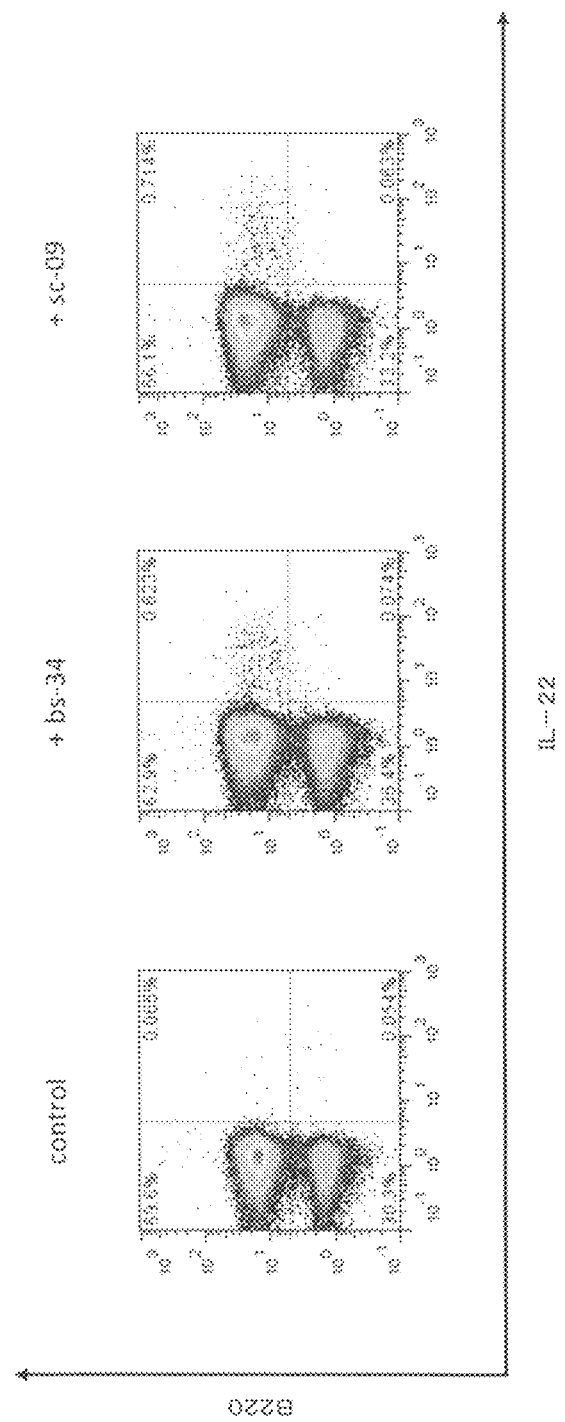
FIG. 7 is a diagram showing a result when measured by flow cytometry on the production inducing potency of IL-22.

FIG. 7 is an example of measurements in the flow cytometry in Example 1, in which the vertical axis represents the expression of B220, the horizontal axis represents the expression of interleukin-22, the control, the case of adding the strain of "bs-34" (*Bacillus subtilis* bs-34) (referred to as "+bs-34"), and the case of adding the strain of "sc-09" (*Bacillus coagulans* sc-09) (referred to as "+sc-09") are shown in order from the left side.

In addition, *Bacillus* bacteria (strains) with high potency to induce the production of IL-22 tended to have high potency to activate B cells. On the other hand, the bacteria with higher B cell activation potency did not necessarily have higher production-inducing capacity for IL-22.

From this fact, it was proven that some *Bacillus* bacteria which can activate B cell by the stimulation of the bacterial cell also possessed IL-22 production inducing potency. If the B cells are in an activated state, an effect of activating immunity can be expected.

In the present embodiment, the B cells were analyzed focusing on B220 positive cells, and similar results were obtained when *lactobacillus* with a higher potency to induce IL-22 production were analyzed with CD19 positive cells (violetFluor450-labeled anti-B220 antibody (manufactured by TONBO Biosciences)) instead of B220 positive cells. From this, it was confirmed that IL-22 production inducing potency from B cells was improved by a predetermined strain, and the activation potency of B cells was further improved.

Example 2

(Measurement Test for Cell Viability and Cell Activation Potency)

With respect to *Bacillus subtilis* bs-30, *Bacillus subtilis* bs-34, and *Bacillus coagulans* sc-09, which exhibited high IL-22 production inducing potency in Example 1, bacterial cells after sterilization were "co-cultured with spleen cells" of experimental mouse (C57BL/6) to investigate the viability of whole spleen cells, the viability of spleen B cells and spleen T cells, and the activation potency of spleen B cells and spleen T cells. Hereinafter, the test content will be described in detail.

(1) Preparation of Bacterial Cell Suspension:

A suspension similar to the suspension of *Bacillus bacterium* prepared in Example 1 was used.

(2) Preparation of Cell Suspension:

Prepared in the same manner as in Example 1.

(3) Cell Culture:

The cell suspension was adjusted with the basic medium so as to be $2 \times 10^6$ cells/mL, and 0.5 mL of the adjusted cell suspension was seeded in 48-well microplate (manufactured by FALCON) to obtain $1 \times 10$ cells/0.5 mL/well.

After that, 5 µL of each bacterial cell suspension (1 mg/mL) was added to each cell suspension and cultured for 2 days under the conditions of 37° C. and 5% $CO_2$. A control was prepared by culturing cell for 2 days without adding the bacterial cell suspension to the adjusted cell suspension under the same conditions (conditions of 37° C. and 5% $CO_2$) as those in which the bacterial cells were added.

(4) Measurement of Cell Viability and Cell Activation Potency:

The cell culture liquid cultured in a 48-well microplate was transferred to a 1.5 mL reaction tube (manufactured by Greiner Bio-One), centrifuged at 1200 rpm for 5 minutes, and the cells were collected. Thereafter, the collected cells were suspended in 0.2 mL of phosphate buffer solution (PBS) of pH6.8, and the following 4 antibodies were added in 1 µL portions and left to stand for 60 minutes in a refrigerator (5° C.).

The 4 antibodies added were violetFluor450-labeled anti-B220 antibody (manufactured by TONBO Biosciences), APC-labeled anti-CD86 antibody (manufactured by TONBO Biosciences), Brilliant Violet510-labeled anti-CD4 antibody (manufactured by BioLegend, Inc.), and PE-labeled anti-CD69 antibody (manufactured by BioLegend, Inc.)

After standing, the cells were centrifuged at 1200 rpm for 5 min, and the cells were collected and suspended in 0.5 mL of phosphate buffer solution (PBS) of pH6.8. Thereafter, 0.5 µL of Propidium Iodide (PI) nucleus staining liquid (manufactured by Cosmo Bio Co., Ltd.) was added to obtain a measuring sample. Measurements were performed on this measuring sample using flow cytometry (MACSQuant Analyzer, manufactured by Milteny Biotec) For the analysis, FCS data analysis software FlowJo (manufactured by FlowJo, LLC) was used.

(Cell Viability)

Among the measuring samples, PI-detected cells (cells stained with PI nucleus staining liquid) were regarded as dead cells, and the difference from the counted number of cells (total number of cells) was regarded as the number of living cells. Then, the ratio of living cells in the total cells (the number of living cells/the number of total cells×100) was calculated. Similarly, the ratio of living cells in total cells in the control (to which no bacterial cell suspension was added) was calculated. Thereafter, these values were compared, and the value of the ratio when the group was taken as the reference (100) was calculated to be the value of the viability of the cell (cell viability). The test was repeated to obtain the mean value ($X^-$) and the standard error (S.E.). The results were shown in Table 4. In this embodiment, "mean value ($X^-$)" is the mean value of six tests (n=6).

(Viability of B Cell)

B cells were detected with violetFluor450-labeled anti-B220 antibody (manufactured by TONBO Biosciences) which is a cell surface marker of B cells. The quotient of the number of B cells among living cells (B220 positive cells among those not detected PI) and the number of total cells (the ratio of the number of viable B cells to the total number of cells) was calculated. Similarly, the ratio of the number of viable B cells to the total number of cells in the control (to which no bacterial cell suspension was added) was calculated. Thereafter, these values were compared, and the value of the ratio when the control was taken as the reference (100) was calculated to be the value of viability of the B cells. The test was repeated to obtain the mean value ($X^-$) and the standard error (S.E.). The results were shown in Table 4.

(Viability of T Cell)

T cells were detected with Brilliant Violet510-labeled anti-CD4 antibody (manufactured by BioLegend, Inc.) which is a cell surface marker of T cells. The quotient of the number of T cells among living cells (CD4 positive cells among those not detected PI) and the number of total cells (the ratio of the number of viable T cells to the number of total cells) was calculated. Similarly, the ratio of the number of viable T cells to the total number of cells in the control (to which no bacterial cell suspension was added) was calculated. Thereafter, these values were compared, and the value of the ratio when the control was taken as the reference (100) was calculated to be the value of viability of the T cell. The test was repeated to obtain the mean value ($X^-$) and the standard error (S.E.). The results were shown in Table 4.

(Activation Potency of B Cell)

B cells expressing B220 and CD86 were detected with violetFluor450-labeled anti-B220 antibody which is a cell surface marker of B cells, and APC-labeled anti-CD86 antibody which is an activation marker of B cells, and the number of B cells was counted. In addition, the quotient of activated B cells ($CD86^+$, $B220^+$) and non-activated B cells ($CD86^-$, $B220^+$) (the value of the ratio of activated B cells to non-activated B cells) among the B cells (B220 positive cells) was calculated. Similarly, the quotient of activated B cells ($CD86^+$, $B220^+$) and non-activated B cells ($CD86^-$, $B220^+$) in control (to which no bacterial cell suspension was added) was calculated. Thereafter, these values were compared, and the value of the ratio when the control was taken as the reference (100) was calculated to be the value of the activation potency of the B cell. The test was repeated to obtain the mean value ($X^-$) and the standard error (S.E.). The results were shown in Table 4.

(Activation Potency of T Cell)

Cells expressing CD4 and CD69 were detected with Brilliant Violet510-labeled anti-CD4 antibody (manufactured by BioLegend, Inc.) which was a cell surface marker of T cells and PE-labeled anti-CD69 antibody (manufactured by BioLegend, Inc.) which was an activation marker of T cells, and the number of cells was counted. In addition, the quotient of activated T cells ($CD69^+$, $CD4^+$) and non-activated T cells ($CD69^-$, $CD4^+$) (the value of the ratio of activated T cells to non-activated T cells) among T cells (CD4 positive cells), was calculated. Similarly, the quotient of activated T cells ($CD69^+$, $CD4^+$) and non-activated T cells (CD69⁻, CD4⁺) in control (to which no bacterial cell suspension was added) was calculated. Thereafter, these values were compared, and the value of the ratio when the control was taken as the reference (100) was calculated to be the value of the activation potency of the T cell. The test was repeated to obtain the mean value ($X^-$) and the standard error (S.E.). The results were shown in Table 4.

TABLE 4

| Strain name | Cell viability $X^-$ | Cell viability S.E. | Viability of B cell $X^-$ | Viability of B cell S.E. | Viability of T cell $X^-$ | Viability of T cell S.E. | Activation potency of B cell $X^-$ | Activation potency of B cell S.E. | Activation potency of T cell $X^-$ | Activation potency of T cell S.E. |
|---|---|---|---|---|---|---|---|---|---|---|
| control | 100 | — | 100 | — | 100 | — | 100 | — | 100 | — |
| Bacillus subtilis bs-30 | 161 | 9 | 149 | 12 | 182 | 8 | 512 | 28 | 208 | 12 |
| Bacillus subtilis bs-34 | 161 | 5 | 151 | 6 | 194 | 11 | 506 | 25 | 210 | 12 |
| Bacillus coagulans sc-09 | 139 | 7 | 132 | 9 | 164 | 11 | 442 | 31 | 199 | 7 |

(Results)

According to the results of this example, it was found that the strain of *Bacillus bacterium* having high IL-22 production inducing potency selected in Example 1 not only has a high activation potency of B cells but also has a high potency to improve the viability of B cells. Furthermore, it was found that the potency to improve the viability of T cells and the activation potency of T cells were also high.

In this embodiment, B cells were analyzed focusing on B220 positive cells, and similar results were obtained when CD19 positive cells (violetFluor450-labeled anti-B220 antibody (manufactured by TONBO Biosciences)) were used instead of B220 positive cells. From this fact, it was confirmed that the viability of the B cell can be improved by the predetermined strain, and the B cell can be further activated.

Example 3

(Measuring Test of Viability of B Cell and Activation Potency of B Cell)

With respect to *Bacillus subtilis* bs-30, *Bacillus subtilis* bs-34, and *Bacillus coagulans* sc-09, which exhibited high IL-22 production inducing potency in Example 1, bacterial cells after sterilization were "co-cultured with spleen-derived B cells (B220 positive cells)" of experimental mouse (C57BL/6), and the potency to improve the viability of spleen B cells and the activation potency of spleen B cells (potency to activate B cells) were investigated. Hereinafter, the measurement test will be described in detail.

(1) Preparation of Bacterial Cell Suspension:

A suspension similar to the suspension of *Bacillus bacterium* prepared in Example 1 was used.

(2) Preparation of B Cell Suspension:

Cells collected from the spleens of experimental mouse (C57BL/6) were collected in 50 ml conical tubes (manufactured by FALCON), and 5 mL of erythrocyte lysis buffer (0.155M $NH_4Cl$, 0.01M Tris-HCl, pH7.5) was added to suspend the cells. Thereafter, 5 mL of phosphate buffer solution (PBS) of pH6.8 was added to this and the mixture was centrifuged at 1200 rpm for 5 minutes. Thereafter, cell suspension was prepared by washing twice with phosphate buffer solution (PBS) of pH6.8.

After suspension in basic medium, a biotin-anti B220 antibody (manufactured by TONBO Biosciences) was added and left to stand for 30 minutes in a refrigerator (5° C.).

After standing, the mixture was centrifuged at 1200 rpm for 5 minutes, washed 2 times with phosphate buffer solution (PBS) of pH6.8, and then suspended in phosphate buffer solution (PBS) of pH6.8. Thereafter, Streptavidin Particles Plus DM, which is a magnetic bead (manufactured by Nippon BD Company, Ltd.) was added, and left to stand for 30 minutes in a refrigerator (5° C.).

Thereafter, the mixture was centrifuged at 1200 rpm for 5 minutes, washed once with phosphate buffer solution (PBS) of pH6.8, and then suspended again in phosphate buffer solution (PBS) of pH6.8 and transferred to a round tube.

Thereafter, cell separation was then carried out using BD IMag Cell Separation System (manufactured by Nippon BD Company, Ltd.), and the cells attracted to the magnet were collected as "B cells (B220 positive cells)" (positive cell fractionation). The collected cells were suspended in basic medium to prepare B cell suspension. The number of cells in the obtained B cell suspension was measured using a hemocytometer.

(3) Cell Culture:

B cell suspension was adjusted in the basic medium so as to be $2\times10^6$ cells/mL, and 1 mL of the adjusted B cell suspension was seeded in a 24-well microplate (manufactured by FALCON) to obtain 2×10 cells/1 ml/well. Thereafter, 10 μl of each bacterial cell suspension was added to each cell suspension, and cultured for 2 days under the condition of 37° C. and 5% $CO_2$. In addition, a control was prepared by culturing cells for 2 days without adding a bacterial cell (bacterial cell suspension) to the adjusted B cell suspension under the same conditions (conditions of 37° C. and 5% $CO_2$) as the level at which the bacterial cell was added.

(4) Measurement of Viability of B Cell and Activation Potency of B Cell:

After culturing, the viability of B cells (the amount of viable B cells) and the activation potency of B cells (the amount of activated B cells) were measured for the respective samples (cell culture liquid) using flow cytometry (MACSQuant Analyzer manufactured by Milteny Biotec).

First, the cell culture liquid that was cultured in a 24-well microplate was transferred to a 1.5 mL reaction tube (manufactured by Greiner Bio-One), centrifuged at 1200 rpm for 5 minutes, and cells were collected. Thereafter, the collected cells were suspended in 0.1 mL of phosphate buffer solution (PBS) of pH6.8, and 0.5 μL of violetFluor450-labeled anti-B220 antibody (manufactured by TONBO Biosciences) and 0.5 μL of APC-labeled anti CD86 antibody (manufactured by TONBO Biosciences) were added, and the mixture was left to stand for 60 minutes in a refrigerator (5° C.)

After standing, the mixture was centrifuged at 1200 rpm for 5 min, and the cells were collected and suspended in 0.5 mL of phosphate buffer solution (PBS) of pH6.8. Thereafter, 0.5 μL of Propidium Iodide (PI) nucleus staining liquid (manufactured by Cosmo Bio Co., Ltd.) was added to obtain a measuring sample. This measuring sample was subjected to measurement using flow cytometry. For the analysis, FCS data analysis software FlowJo (manufactured by FlowJo, LLC) was used.

(Viability of B Cell)

Among the measuring samples, PI detected cells (cells stained with PI nucleus staining liquid) were regarded as dead cells, and the difference from the counted number of cells (total number of cells) was regarded as the number of living cells. Then, the ratio of living cells in the total cells (the number of living cells/the number of total cells×100) was calculated. Similarly, the ratio of living cells in total cells in the control (to which no suspension of *Bacillus bacterium* was added) was calculated. Thereafter, these values were compared, and the value of the ratio when the control was taken as the reference (100) was calculated to be the value of the viability of B cells (cell viability). The test was repeated to obtain the mean value ($X^-$) and the standard error (S.E.). The results are shown in "Viability of B cell" in Table 5. In this embodiment, "mean value ($X^-$)" is the mean value of four tests (n=4).

(Activation Potency of B Cell)

B cells expressing B220 and CD86 were detected with violetFluor450-labeled anti-B220 antibody which is a cell surface marker of B cells, and APC-labeled anti-CD86 antibody which is an activation marker of B cells, and the number of B cells was counted. In addition, the quotient of activated B cells (CD86$^+$, B220$^+$) and non-activated B cells (CD86$^-$, B220$^+$) (the ratio of the number of activated B cells to the number of non-activated B cells) among B cells (B220 positive cells), was calculated. Similarly, the quotient of activated B cells (CD86$^+$, B220$^+$) and non-activated B cells (CD86$^-$, B220$^+$) in control (to which no bacterial cell suspension was added) was calculated. Thereafter, these values were compared, and the value of the ratio when the control was taken as the reference (100) was calculated to be the value of the activation potency of the B cell. The test was repeated to obtain the mean value ($X^-$) and the standard error (S.E.). The results are shown in "Activation potency of B cell" in Table 5.

TABLE 5

| Strain name | Viability of B cell | | Activation potency of B cell | | IL-22 production inducing potency | |
|---|---|---|---|---|---|---|
| | $X^-$ | S.E. | $X^-$ | S.E. | $X^-$ | S.E. |
| control | 100 | — | 100 | — | 100 | — |
| *Bacillus subtilis* bs-30 | 370 | 38 | 217 | 26 | 734 | 49 |
| *Bacillus subtilis* bs-34 | 340 | 57 | 234 | 24 | 745 | 10 |
| *Bacillus coagulans* sc-09 | 500 | 27 | 220 | 6 | 1,089 | 183 |

(Results)

According to the results of this example, it was further confirmed that the "strain having high IL-22 production inducing potency" selected in Example 1 was able to directly act on B cells to improve the viability of B cells and activate B cells.

Example 4

(Measuring Test for IL-22 Production Inducing Potency of B Cell)

With respect to *Bacillus subtilis* bs-30, *Bacillus subtilis* bs-34, and *Bacillus coagulans* sc-09, which exhibited high IL-22 production inducing potency in Example 1, bacterial cells after sterilization were "co-cultured with B cells (B220 positive cells) derived from spleens" of experimental mouse (C57BL/6), to investigate IL-22 production inducing potency. Hereinafter, the measurement test will be described in detail.

(1) Preparation of Bacterial Cell Suspension:

A suspension similar to the suspension of *Bacillus bacterium* prepared in Example 1 was used.

(2) Preparation of B Cell Suspension: Prepared as in Example 3

(3) Cell Culture: Cultured in the Same Manner as in Example 3

(4) Measurements of IL-22:

After 42 hours of cultivation, 0.67 μL of BD GolgiStop (manufactured by BD) was added to the each culture liquid and mixed. Thereafter, the culture liquids were cultured at 37° C. and 5% $CO_2$ for 6 hours.

Thereafter, the cell culture liquid cultured in a 24-well microplate (manufactured by FALCON) was transferred to a 1.5 mL reaction tube (manufactured by Greiner Bio-One), centrifuged at 1200 rpm for 5 minutes, and cells were collected. After that, the collected cells were fixed and permeated by using BD Cytofix/Cytoperm™ Fixation/Permeabilization Kit (manufactured by BD). This procedure followed the instructions attached to Fixation/Permeabilization Kit.

For staining of B cells, violetFluor450-labeled anti-B220 antibody (manufactured by TONBO Biosciences) was used. In addition, for staining of IL-22, PE-labeled anti-IL-22 antibody (manufactured by affymetrix eBioscience) was used.

Staining reaction was performed by being left to stand for 60 minutes in a refrigerator (5° C.). Thereafter, the mixture was centrifuged at 1200 rpm for 5 minutes, and the cells were collected and suspended in 0.5 mL of phosphate buffer solution (PBS) of pH6.8 to obtain a measuring sample. This measuring sample was subjected to measurement using flow cytometry. For the analysis, FCS data analysis software FlowJo (manufactured by FlowJo, LLC) was used.

The ratio of IL-22 positive cells in B cells (IL-22$^+$, B220$^+$/B220$^+$) was determined for respective measuring sample, and the ratio of IL-22 positive cells in B cells in the control (to which no bacterialcell suspension was added) was taken as the standard (100), and the relative value of respective measuring sample was calculated to be the value of IL-22 production cell amount of B cells. The test was repeated to obtain the mean value ($X^-$) and the standard error (S.E.). The results are shown in "IL-22 production inducing potency" in Table 5. In this embodiment, "mean value ($X^-$)" is the mean value of four tests (n=4).

(Results)

According to the results of this example, it was found that the "strain having a high IL-22 production inducing potency" selected in Example 1 directly acted on B cells and increased B cells producing IL-22.

Example 5

(Feeding Test (Normal Mouse))

Experimental mouse was ingested with a bacterial cell after sterilization of "*Bacillus coagulans* sc-09," which had a high IL-22 production inducing potency, and then the skin condition was measured (TransEpidermal Water Loss (TEWL)). In addition, a group to which IL-22 was administered ("IL-22 administered group" in Table 6) and a group to which IL-22 neutralizing antibody was administered ("Bacterial cell ingested/Anti-IL-22 antibody administered group" in Table 6) were also prepared, and skin changes due to IL-22 inoculation were also confirmed.

(1) Preparation of *Bacillus bacterium* Mixed Feed:

A feed (*Bacillus bacterium* mixed feed) was prepared by containing 1 w/w % bacterial cells of *Bacillus coagulans* sc-09, which were sterilized and then lyophilized, in a general feed for mouse. As a general feed for mouse, a mouse breeding feed CE-2 (manufactured by CLEA Japan, Inc.) was used.

(2) Feeding Breeding:

Twelve general experimental mice (C57BL/6) (8-week-old females) were divided into four groups (three per group), wherein two groups were fed with the *Bacillus bacterium* mixed feed and the other two groups were fed with general feed for mouse not containing bacterial cells of *Bacillus bacterium*, and they were bred for 21 days.

One of the two groups fed with general feed for mouse not containing bacterial cells of *Bacillus bacterium* was injected IL-22 recombinant proteins "Recombinant IL-22 (Recombinant Mouse IL-22 manufactured by TONBO Biosciences)" into the tail vein (2 μg/mouse each) after 14 days and 17 days from the start of the feeding, respectively. Among the above two groups, the group in which the "Recombinant IL-22" was injected into the tail vein was referred to as the "IL-22 administered group", and the group in which the "Recombinant IL-22" was not injected (administered) into the tail vein was referred to as the "Control group".

One of the two groups fed with the *Bacillus bacterium* mixed feed was injected "Anti-IL-22 Antibody (IL-22 Monoclonal Antibody manufactured by Thermo Fisher)" as a IL-22 neutralizing antibody into the tail vein (20 μg/mouse each) after 14 days and 17 days from the start of the feeding, respectively. Among the above two groups, the group in which "Anti-IL-22 antibody" was injected into the tail vein was referred to as the "Bacterial cell ingested/Anti-IL-22 antibody administered group" and the group in which "Anti-IL-22 antibody" was not injected (administered) into the tail vein was referred to as the "Bacterial cell ingested group".

(3) Measurements of Transepidermal Water Loss (TEWL):

After 21 days from the start of the feeding, the transepidermal water loss (TEWL) of the skin on the back of the mouse in each group was measured. In this measurement, the back of the mouse was shaved the day before (day 20). TEWL was measured by a skin measuring device "DermaLab®" manufactured by CORTEX TECHNOLOGY. TEWL was measured three times in each mouse, the mean value was obtained, and the mean value and the standard deviation of each group were obtained. The results of transepidermal water loss (TEWL) were shown in Table 6 and FIG. 8. The numerical values of the control group and each other group were subjected to F-test to confirm whether or not there was a significant difference in variance. A Student's t-test, which is a two-sample test assuming equal variance, was then performed.

TABLE 6

| TEWL (g/m$^2$/h) | Control group | Bacterial cell ingested group | IL-22 administered group | Bacterial cell ingested/Anti-IL-22 antibody administered group |
|---|---|---|---|---|
| Mean value | 63.5 | 32.2 | 40.6 | 82.8 |
| Standard deviation | 2.3 | 4.3 | 5.5 | 4.6 |
|  |  | p = 0.0004 | p = 0.003 | p = 0.003 |

Figure 8:
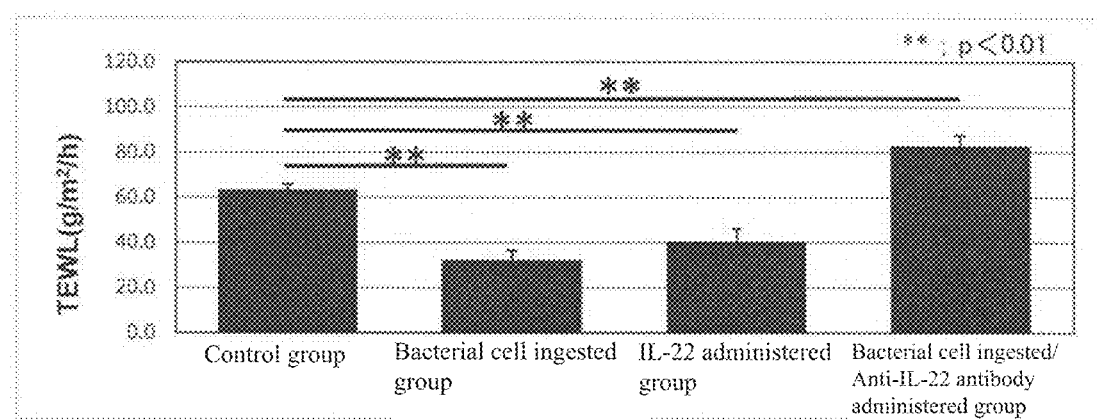
FIG. 8 is a graph showing a measurement result of the transepidermal water loss (TEWL) in Example 5.

As is clear from the results of Table 6 and FIG. 8, TEWL was lower in the bacterial cell ingested group (the group ingesting "*Bacillus coagulans* sc-09" and not administering "Anti-IL-22 antibody") than in the control group, and p<0.01 (p=0.0004) was obtained as a result of Student's t-test, which was significantly different at the significance level of 1%.

As can be seen from Table 6, TEWL was lower in IL-22 administered group (the group administering IL-22 without *Bacillus bacterium* mixed feed) than in the control group, and p<0.01 (p=0.003) was obtained as a result of Student's t-test, which was significantly different at the significance level of 1%. In addition, TEWL was higher (i.e., the transpiration rate of water from the skin was higher) in the "Bacterial cell ingested/Anti-IL-22 Antibody administered group" than in the bacterial cell ingested group, and in the control group, and p<0.01 (p=0.003) was obtained as a result of Student's t-test, which was significantly different at the significance level of 1%. No changes in skin conditions were visually observed in the mice of each group.

Thus, according to this embodiment, it was found that TEWL was lowered in the bacterial cell ingested group, and that the barrier function of the skin was enhanced by ingestion of the *Bacillus bacterium* of the present invention.

While TEWL was decreased by the administration of IL-22, it was confirmed that IL-22 enhanced the barrier function of the skin because TEWL was increased by the administration of neutralizing antibody of IL-22 (injected into the tail vein) (see Table 6 and FIG. 8). And, the improvement of the barrier function of the skin by the ingestion of bacterial cell is based on the stimulation caused by the ingestion of the bacterial cell, and it may be based on the production inducing of IL-22 by the bacterial cell.

Example 6

(Feeding Test (Sterile Mouse))

Sterile mouse was ingested with a bacterial cell after sterilization of "*Bacillus subtilis* bs-34" which had high IL-22 production inducing potency, and then the skin condition was measured (TransEpidermal Water Loss (TEWL)).

(1) Preparation of Bacterial Cell Mixed Feed:

A feed (*Bacillus bacterium* mixed feed) was prepared by containing 1 w/w % bacterial cells of *Bacillus subtilis* bs-34, which were sterilized and then lyophilized, in a general feed for mouse. As a general feed for mouse, a mouse breeding feed CE-2 (manufactured by CLEA Japan, Inc.) was used.

(2) Feeding Breeding:

Ten sterile mice (C57BL/6NJcl [Gf]) (8-week-old females) were divided into the groups of five, wherein one group was fed with the *Bacillus bacterium* mixed feed (Bacterial cell ingested group) and another group was fed with the general feed for mouse not containing bacterial cells (Control group), and they were bred in a sterile environment for one month.

Figure 9:
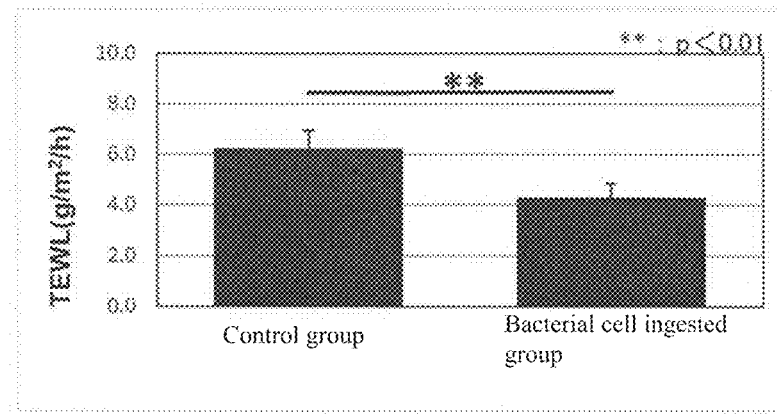
FIG. 9 is a graph showing a measurement result of the transepidermal water loss (TEWL) in Example 6.

(3) Measurements of Transepidermal Water Loss (TEWL):

After 1 month from the start of the feeding, TEWL in the skin of the back was measured. Immediately before the measurement, the back of the mouse was shaved with a hair clipper for a small animal, and then the measurement was performed. TEWL was measured by a skin measuring device "DermaLab®" manufactured by CORTEX TECHNOLOGY. TEWL was measured three times in each mouse and the mean value and standard deviations were determined. The results are shown in Table 7 and FIG. 9. The numerical values of the control group and the bacterial cell ingested group were subjected to F-test to confirm whether or not there was a significant difference in variance. Thereafter, a Student's t-test was performed.

TABLE 7

| TEWL (g/m$^2$/h) | Control group | Bacterial cell ingested group |
|---|---|---|
| Mean value | 6.2 | 4.3 |
| Standard deviation | 0.7 | 0.5 |
|  |  | p = 0.001 |

The bacterial cell ingested group had significantly lower TEWL than the control group (group not ingested *Bacillus bacterium* mixed feed), and the results of Student's t-test showed p<0.01 (p=0.001), with significant differences at the significance level of 1%. As described above, it was also found from this embodiment that TEWL was low in the bacterial cell ingested group, and that the barrier function of the skin was enhanced by ingestion of the *Bacillus bacterium* of the present invention.

As described above, it was found that the *Bacillus bacterium* of the present invention has a high IL-22 production inducing potency. Furthermore, it has been found that the *Bacillus bacterium* of the present invention have the potency to improve the viability of B cells by directly acting on B cells, and have the activation potency of B cells. From this result, it can be seen that the *Bacillus bacterium* of the present invention has an immunostimulatory action. It has also been found that *Bacillus bacterium* of the present invention enhance (potentiate) the barrier function of the skin.

INDUSTRIAL APPLICABILITY

The *Bacillus bacterium* of the present invention can be employed as an active ingredient of a IL-22 production inducing agent (further, an active ingredient of a skin barrier function enhancing agent) by being added to food and drink, supplement, medicine, or the like to produce IL-22, or the *Bacillus bacterium* of the present invention may be used itself as a food and drink, a supplement, a medicine, or the like. Examples of food and drinks include *miso*, instant *miso* soup, cooked *miso* (processed *miso* products), name-*miso* such as Kinzanji *miso*, soy sauce, soup, season sauce, seasoning sauce, seasoning for rice, side dishes, and sweet rice drinks (yeast drinks).

Accession Number
    Accession number NITE BP-02583
    Date of Accession: Dec. 5, 2017
    Accession Institution: NITE Patent Microorganisms Depositary, National Institute of Technology and Evaluation
    Accession Institution Address: Room 122, 2-5-8 Kazusakamatari, Kisarazu-shi, Chiba 292-818, Japan
    Accession number NITE BP-02584
    Date of accession: Dec. 5, 2017
    Accession Institution: NITE Patent Microorganisms Depositary, National Institute of Technology and Evaluation
    Accession Institution Address: Room 122, 2-5-8 Kazusakamatari, Kisarazu-shi, Chiba 292-818, Japan
    Accession number NITE BP-02590
    Date of accession: Dec. 5, 2017
    Accession Institution: NITE Patent Microorganisms Depositary, National Institute of Technology and Evaluation
    Accession Institution Address: Room 122, 2-5-8 Kazusakamatari, Kisarazu-shi, Chiba 292-818, Japan

The invention claimed is:

1. A method for inducing interleukin-22 production in a subject, comprising:
    administering a *Bacillus bacterium* to a subject, wherein the *Bacillus bacterium* induces the production of interleukin-22;
    wherein the *Bacillus bacterium* is a *Bacillus bacterium* of Accession number NITE BP-02583, a *Bacillus bacterium* of Accession number NITE BP-02584, or a *Bacillus bacterium* of Accession number NITE BP-02590.

2. The method according to claim 1, wherein the *Bacillus bacterium* has the potency to improve the viability of B cells and the activation potency of B cells.

3. The method according to claim 1, wherein the *Bacillus bacterium* is derived from foods.

4. The method according to claim 1, wherein the *Bacillus bacterium* is derived from *miso* or *natto*.

5. The method according to claim 2, wherein the *Bacillus bacterium* is derived from foods.

6. The method according to claim 2, wherein the *Bacillus bacterium* is derived from *miso* or *natto*.

* * * * *

SEQUENCE LISTING

```
Sequence total quantity: 2
SEQ ID NO: 1              moltype = DNA  length = 16
FEATURE                   Location/Qualifiers
misc_feature              1..16
                          note = Primer 1
source                    1..16
                          mol_type = other DNA
                          organism = synthetic construct
SEQUENCE: 1
gtttgatcct ggctca                                                 16

SEQ ID NO: 2              moltype = DNA  length = 16
FEATURE                   Location/Qualifiers
misc_feature              1..16
                          note = Primer 2
source                    1..16
                          mol_type = other DNA
                          organism = synthetic construct
SEQUENCE: 2
taccttgtta cgactt                                                 16
```